United States Patent [19]

Feuer et al.

[11] Patent Number: 4,563,479

[45] Date of Patent: Jan. 7, 1986

[54] SYNERGISTIC RADIATION PROTECTIVE PHARMACEUTICAL COMPOSITIONS

[75] Inventors: László Feuer; György Benko, both of Budapest, Hungary

[73] Assignee: Chinoin Gyogyszer es Vegyeszeti Termekek Gyar RT, Budapest, Hungary

[21] Appl. No.: 571,856

[22] Filed: Jan. 18, 1984

Related U.S. Application Data

[63] Continuation of Ser. No. 133,832, Mar. 25, 1980, abandoned.

[30] Foreign Application Priority Data

Apr. 2, 1979 [HU] Hungary ............................ CI 1924

[51] Int. Cl.[4] .......................................... A61K 31/195
[52] U.S. Cl. ................................... 514/562; 514/631; 514/917
[58] Field of Search .................... 514/562, 631, 917

[56] References Cited

FOREIGN PATENT DOCUMENTS

| 828546 | 4/1975 | Belgium . |
| 854347 | 5/1977 | Belgium . |
| 1504541 | 3/1978 | United Kingdom . |
| 1574950 | 9/1980 | United Kingdom . |

OTHER PUBLICATIONS

Feuer et al., Effect of Glutaurine and Its Derivatives and Their Combinations with Known Radio-Protective Substances Upon Irradiated Mice, undated article/apparently unpublished.
Benko et al., "Investigation of the Radiation Protection Effect of Litoralon $^R$/Gamma-L-Glutamyl Taurine/in Experimental Animals", undated article/apparently unpublished.
Merck Index, 9th ed. (1976), entry 2777.
Chemical Abstracts 84:126754b (1976).
Kaluszyner, Radiation Res. 14 (1961), pp. 23–28.
Knoll, Gyogyszertan, Medicina, (1965), pp. 540–541.

*Primary Examiner*—Leonard Schenkman
*Attorney, Agent, or Firm*—Karl F. Ross; Herbert Dubno

[57] ABSTRACT

The invention is directed to a synergistic radiation protective pharmaceutical composition comprising 50 to 350 parts by weight of aminoalkyl-thiol-derivatives of the general formula II

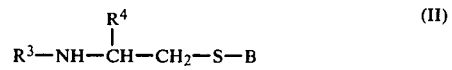

wherein
$R^3$ stands for hydrogen, or carboxamidino
$R^4$ stands for hydrogen or carboxy,
B represents hydrogen or carboxamidino with the restriction that at least two of $R^3$, $R^4$ and B stand for hydrogen— or a pharmaceutically acceptable acid addition salt thereof, 0.2 to 2 parts by weight of ω-acylamino-alkane-derivative of the general formula

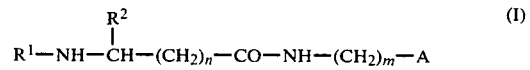

wherein
$R^1$ stands for hydrogen, $C_{1-4}$ alkanoyl, aroyl or aryl-($C_{1-4}$)-alkoxy-carbonyl,
$R^2$ stands for hydrogen, or carboxy optionally esterified by $C_{1-4}$ alkoxy or aryl-($C_{1-4}$)alkoxy,
A stands for —$SO_2OH$ or —O—$PO(OH)_2$,
n stands for 1, 2 or 3 and
m stands for 2, 3 or 4—or a pharmaceutically acceptable salt thereof, and pharmaceutically acceptable carriers, diluents and/or solvents, and/or other formulating excipients.

1 Claim, No Drawings

SYNERGISTIC RADIATION PROTECTIVE PHARMACEUTICAL COMPOSITIONS

This application is a continuation of application Ser. No. 133,832, filed Mar. 25, 1980, now abandoned.

FIELD OF THE INVENTION

The present invention relates to synergistic radiation protective pharmaceutical compositions and a process for the preparation thereof.

BACKGROUND OF THE INVENTION

It is known that aminoalkyl-thiol derivatives of the formula II

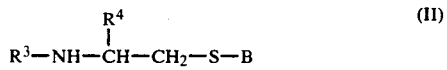

containing a sulfhydryl group—wherein
$R^3$ is hydrogen or carboxamidino
$R^4$ is hydrogen or carboxy and
B is hydrogen or carboxamidino, provided that at least two of $R^3$ and $R^4$ and B are hydrogen-
and pharmaceutically acceptable acid addition salts thereof are the most effective radiation-protective substances known heretofore (Knoll J., Gyógyszertan, Medicina, 1965, page 540). As examples for the above substances cysteine, cysteamine, aminoethyl-isothiuronium-chloride-hydrochloride, aminoethyl-isothiuronium-bromide-hydrobromide and mercaptoethyl-guanidine may be mentioned. Though the radiation protective activity of the above substances is significant in animal tests, the practical therapeutic utilization thereof is rather difficult because of the toxicity of their effective dose or because this effective dose is rather close to the toxic range.

Some of the characteristics of some most important radiation protective active ingredients are shown in Table 1.

TABLE 1

| Active ingredient | $LD_{50}$ p.o. mg./kg. | Radiation protective dose mg./kg. | Therapeutic index |
|---|---|---|---|
| cysteine-hydrochloride | 2500 | 1900 | 1.31 |
| aminoethyl-isothiuronium-bromide-hydrobromide | 1200 | 1000 | 1.20 |
| aminoethyl-isothiuronium-chloride-hydrochloride | 710 | 400 | 1.78 |
| mercaptoethyl-guanidine | 350 | 200 | 1.75 |

The data of the table show that the toxic and therapeutic doses are close to each other.

With the increasing use of radioactive isotopes the probability of radiation injuries increases as well. As a consequence radiation-protective pharmaceutical compositions are needed more and more. In this field both compositions suitable for curing radiation injuries and compositions suitable for treating humans or animals prior to irradiation in order to increase the tolerated dose by the patients for cases of higher radiation doses are desired.

DESCRIPTION OF THE INVENTION

It has been surprisingly found that a combination of known aminoalkyl thiol derivatives or acid-addition salts thereof of the formula II with known ω-acylamino-alkane-derivatives of the formula I

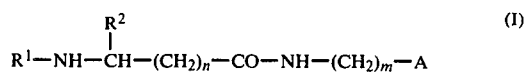

wherein
$R^1$ is hydrogen or $C_{1-4}$ alkanoyl, aroyl, aryl($C_{1-4}$)-alkoxy-carbonyl,
$R^2$ is hydrogen or a carboxy group which can be esterified with aryl-($C_{1-4}$)alkoxy,
A is $-SO_2OH$ or $-O-PO(OH)_2$,
n is 1, 2 or 3 and
m represents 2, 3 or 4
or a pharmaceutically acceptable salt thereof (Belgian Patent Specification 828 546 and 854 347) possesses unexpected synergistic activity and even if compounds of the formula II are used in a less toxic dose a good radiation protective effect is obtained.

Some representatives of the compounds of the formula I are γ-glutamyltaurine, γ-glutamylhomotaurine, γ-glutamylcholamine phosphate, γ-aspartyltaurine, β-aspartylhomotaurine, β-aspartylcholamine phosphate, aminobutyryltaurina, aminobutyrylcholamine phosphate and aminobutyrylhomotaurine aminobutyryltaurine, aminobutyrylhomotaurine, aminobutyrylcholamine sulfate, aminoisobutyryltaurine, aminoisobutyrylhomotaurine or aminoisobutyrylcholamine phosphate.

The synergistic radiation protective pharmaceutical compositions according to the invention contain 0.02 to 2 parts by weight of a compound of the formula I or a salt thereof and 50 to 350 parts by weight of the aminoalkyl-thiol derivative of the formula II or a salt thereof, and the conventionally used carriers, diluents, optionally coloring-, flavoring-, stabilizing- and/or formulating agents.

The dosage units, such as tablets, capsules, suppositories, injectable solutions or infusions contain preferably 100 to 200 mg. of the compound of the formula II or a salt thereof and 0.01 to 2 mg. of the compound of the formula I or a salt thereof.

The pharmaceutical compositions may be prepared by using formulating excipients, such as solid, liquid and semi-liquid carriers, such as methyl cellulose, starch, various sugars, e.g. lactose, sucrose, sugar alcohols, such as sorbitol, mannitol and as lubricants e.g. magnesium stearate, talc, calcium stearate etc. may be used. As liquid carriers water, lower alcohols may be used alone or in combination with each other or with the carriers mentioned above. The suppository masses are used as semi-liquid carriers for the preparation of suppositories.

The compositions may further contain stabilizers, fungicidal agents, antioxidants, aromas, flavoring agents, pH-adjusters, osmotic pressure controlling components, such as various buffers and sodium chloride.

The tablets prepared from compositions according to the invention may be coated with shellac, which may optionally be suitably colored, and thus intestino-solvent tablets are obtained. The same effect may be achieved by granulating the active ingredients and other necessary additives and by enclosing the obtained granules into capsules which resist the gastric acid, dissolve in the alkaline medium of the intestinal tract or by coating the obtained granules with a suitable coating.

The synergistic pharmaceutical compositions may also be prepared in the form of lyophilized injectable compositions containing the active ingredient combination in the form of a solid powder mixture. The injectable solution is prepared prior to administration by methods known per se from the compositions mentioned above by using a solvent, such as sterile water, or physiological saline solution.

The synergistic activity of the active ingredient combinations is shown in Table 2. Experiments are carried out in mice. Irradiation was carried out with X-ray (rtg) and with gamma rays obtained from $^{60}$Co isotope. Survival was observed on the 30th day after irradiation and expressed by using survival coefficient "S" according to Kaluszyner. (Rad. Res., 27, 518, 1961). Mice were treated intraperitoneally.

TABLE 2

| Treatment physiological | Irradiation | | Survival | |
|---|---|---|---|---|
| | rtg (R) | gamma (rad) | % | "S" |
| physiological saline | 630 | | 0 | 0.30 |
| physiological saline | | 900 | 0 | 0.34 |
| physiological saline | 800 | | 0 | 0.24 |
| physiological saline | | 1100 | 0 | 0.20 |
| 140 mg./kg. AET + Litoralon 100 μg/kg. | 630 | | 56 | 0.48 |
| 140 mg./kg. AET + Litoralon 100 μg/kg. | | 900 | 67 | 0.80 |
| 140 mg./kg. AET + Litoralon 100 μg./kg. | 800 | | 48 | 0.40 |
| 140 mg./kg. AET + Litoralon 100 μg./kg. | | 1100 | 51 | 0.78 |
| 140 mg./kg. AET + Litoralon 1 mg./kg. | 630 | | 68 | 0.82 |
| 140 mg./kg. AET + Litoralon 1 mg./kg. | | 900 | 71 | 0.89 |
| 140 mg./kg. AET + LItoralon 1 mg./kg. | 800 | | 54 | 0.40 |
| 140 mg./kg. AET + Litoralon 1 mg./kg. | | 1100 | 61 | 0.75 |

In the Table 3 survival and factor "S" of the mice treated only with AET are shown for the sake of comparison. The Table 3 shows that 140 mg./kg. of AET alone substantially does not give any radiation protection.

TABLE 3

| Treatment | Irradiation | | Survival | |
|---|---|---|---|---|
| i.p. | rtg (R) | gamma (rad) | % | "S" |
| 140 mg./kg. AET alone | 630 | | 15 | 0.39 |
| " | | 900 | 5 | 0.37 |
| " | 800 | | 0 | 0.27 |
| " | | 1100 | 0 | 0.28 |

Similar good results may be obtained as according to Table 2 by employing other compounds of the formula I. The results are shown in Table 4.

TABLE 4

| Treatment | Irradiation | Survival | |
|---|---|---|---|
| i.p. | gamma (rad) | % | "S" |
| 140 mg./kg. AET + 100 μg./kg GABA-T | 900 | 60.7 | 0.71 |
| 140 mg./kg. AET + 100 μg./kg GABA-T | 1100 | 39.8 | 0.38 |
| 140 mg./kg. AET + 100 μg./kg. GABE-E | 900 | 61.0 | 0.75 |
| 140 mg./kg. AET + 100 μg./kg. GABE-E | 1100 | 38.6 | 0.35 |

Abbreviations in the Tables are as follows:

AET=aminoethyl-isothiuronium-chloride-hydrochloride Litoralon=γ-glutamyl-taurine
GABA-T=γ-aminobutyryl-taurine
GABA-E=γ-aminobutyryl-ethanolamine-phosphate
140 mg./kg. AET dose used according to the above tables is the half of the radiation protective dose used in mice i.p.

TABLE 5

Radiation-protective activity of a combination of Litoralon and mercapto alkyl amine with irradiation being carried out with cobalt 60 gamma.
Dose ouput: 55.5 rad/min.
20 animals in each group.

| Test substance and dose | Radiation dose | Survival % 30. day | "S" |
|---|---|---|---|
| Control physiological saline solution: 0.5 ml. | LD$_{50/30}$ | 50.0 | 0.61 |
| Control physiological saline solution: 0.5 ml. | LD$_{100/30}$ | 0 | 0.28 |
| Litoralon 100 μg/kg. + 1000 mg/kg. cysteine | LD$_{50/30}$ | 100.0 | 1.0 |
| Litoralon 100/μg./kg. + 1000 mg/kg. cysteine | LD$_{100/30}$ | 66.7 | 0.88 |
| Litoralon 100 μg./kg. + cystamine 150 mg./kg. | LD$_{50/30}$ | 70.1 | 0.89 |
| Litoralon 100 μg./kg. + cystamine 150 mg./kg. | LD$_{100/30}$ | 83.3 | 0.91 |
| Litoralon 100 μg./kg. + cystamine 150 mg./kg. | LD$_{50/30}$ | 100.0 | 1.0 |
| Litoralon 100 μg./kg. + cystamine 150 mg./kg. | LD$_{100/30}$ | 89.0 | 0.92 |

The synergistic radiation protective pharmaceutical compositions may be employed not only prior to irradiation but after irradiation as well. In latter case the radiation injuries of the central nervous system and of the intestinal mucosa are favorably influenced. The decrease of output and the occurrance of muscle coordination disorders are inhibited or remedied by the compositions as shown by the animal-tests carried out on a rotating and standing rod. Opticovestibular injuries (nistagmus tendency) are controlled.

SPECIFIC EXAMPLES

Further details of the invention are illustrated by the following Examples, which serve merely as illustration and not for restriction.

EXAMPLE 1

Tablets are prepared having the following composition: 200 mg. cysteamine-hydrochloride
0.1 mg. γ-glutamyl-taurine
120 mg. mannitol
20 mg. magnesium stearate
100 mg. wheat starch

EXAMPLE 2

Tablets are prepared having the following composition:
100 mg. aminoethyl-isothiuronium-chloride-hydrochloride
0.2 mg. γ-aminobutyryl-ethanolamine-phosphate
100 mg. mannitol
50 mg. methyl cellulose
50 mg. wheat starch
15 mg. magnesium stearate
10 mg. talc